(12) United States Patent
Lafontaine et al.

(10) Patent No.: US 7,854,755 B2
(45) Date of Patent: *Dec. 21, 2010

(54) VASCULAR CATHETER, SYSTEM, AND METHOD

(75) Inventors: Daniel M. Lafontaine, Plymouth, MN (US); Mark L. Jenson, Greenfield, MN (US); William J. Drasler, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 646 days.

This patent is subject to a terminal disclaimer.

(21) Appl. No.: 11/049,000

(22) Filed: Feb. 1, 2005

(65) Prior Publication Data

US 2006/0173475 A1 Aug. 3, 2006

(51) Int. Cl.
   *A61F 2/06* (2006.01)
   *A61F 2/24* (2006.01)
(52) U.S. Cl. .................... 623/1.11; 623/2.11; 606/170
(58) Field of Classification Search ........... 623/1.11, 623/2.11, 2.13, 2.14, 1.24; 604/22; 606/108, 606/166, 167, 170, 171, 159, 200, 192, 191
   See application file for complete search history.

(56) References Cited

U.S. PATENT DOCUMENTS

| | | | |
|---|---|---|---|
| 3,671,979 A | 6/1972 | Moulopoulos | 3/1 |
| 4,291,420 A | 9/1981 | Reul | 3/1.5 |
| 4,787,901 A | 11/1988 | Baykut | 623/2 |
| 4,872,874 A | 10/1989 | Taheri | 623/1 |
| 4,935,030 A | 6/1990 | Alonso | 623/2 |
| 4,994,077 A | 2/1991 | Dobben | 623/2 |
| 5,002,567 A | 3/1991 | Bona et al. | 623/2 |
| 5,141,491 A | 8/1992 | Bowald | 604/22 |
| 5,163,953 A | 11/1992 | Vince | 623/2 |
| 5,219,355 A | 6/1993 | Parodi et al. | 606/191 |

(Continued)

FOREIGN PATENT DOCUMENTS

DE        849 592        9/1952

(Continued)

OTHER PUBLICATIONS

US 6,673,110, 01/2004, Alfieri et al. (withdrawn)

(Continued)

*Primary Examiner*—Anhtuan T Nguyen
*Assistant Examiner*—Amy Lang
(74) *Attorney, Agent, or Firm*—Brooks, Cameron & Huebsch, PLLC

(57) ABSTRACT

A catheter including an elongate body, a first cutting head and a second cutting head both having a blade, where the blades moves relative each other to provide a shearing action for cardiac tissue. The catheter can further include a stent positioned over an inflatable balloon, where the inflatable balloon can deploy the expandable stent over sheared cardiac tissue. The catheter can further be included in a system having a sheath, where at least a part of the catheter resides in the lumen of the sheath. The sheath further includes a cardiac valve and an expandable filter. The sheath can move relative the cardiac valve and the expandable filter to deploy the cardiac valve and at least a portion of the expandable filter proximal the inflatable balloon and the expandable stent.

10 Claims, 5 Drawing Sheets

U.S. PATENT DOCUMENTS

| | | | |
|---|---|---|---|
| 5,254,127 A | 10/1993 | Wholey et al. | 606/153 |
| 5,327,774 A | 7/1994 | Nguyen et al. | 73/37 |
| 5,332,402 A | 7/1994 | Teitelbaum | 623/2 |
| 5,370,685 A | 12/1994 | Stevens | |
| 5,411,552 A | 5/1995 | Andersen et al. | 623/2 |
| 5,469,868 A | 11/1995 | Reger | 128/898 |
| 5,480,423 A | 1/1996 | Ravenscroft et al. | 623/1 |
| 5,500,014 A | 3/1996 | Quijano et al. | 623/2 |
| 5,545,214 A | 8/1996 | Stevens | 623/2 |
| 5,554,185 A | 9/1996 | Block et al. | 623/2 |
| 5,643,208 A | 7/1997 | Parodi | 604/96 |
| 5,693,087 A | 12/1997 | Parodi | 623/1 |
| 5,713,953 A | 2/1998 | Vallana et al. | 623/2 |
| 5,716,370 A | 2/1998 | Williamson, IV et al. | 606/153 |
| 5,735,859 A | 4/1998 | Fischell et al. | 606/108 |
| 5,741,326 A | 4/1998 | Solovay | 623/1 |
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,840,081 A | 11/1998 | Andersen et al. | |
| 5,879,320 A | 3/1999 | Cazenave | 604/8 |
| 5,895,419 A | 4/1999 | Tweden et al. | 623/2 |
| 5,910,170 A | 6/1999 | Reimink et al. | 623/2 |
| 6,010,531 A | 1/2000 | Donlon et al. | 623/2 |
| 6,042,607 A | 3/2000 | Williamson, IV et al. | 623/2 |
| 6,139,575 A | 10/2000 | Shu et al. | 623/2.12 |
| 6,287,334 B1 | 9/2001 | Moll et al. | 623/1.24 |
| 6,312,447 B1 | 11/2001 | Grimes | 606/219 |
| 6,355,030 B1 | 3/2002 | Aldrich et al. | 606/28 |
| 6,390,098 B1 * | 5/2002 | LaFontaine et al. | 128/898 |
| 6,402,780 B2 | 6/2002 | Williamson, IV et al. | 623/2.11 |
| 6,419,696 B1 | 7/2002 | Ortiz et al. | 623/2.37 |
| 6,425,916 B1 | 7/2002 | Garrison et al. | 623/2.11 |
| 6,440,164 B1 | 8/2002 | DiMatteo et al. | 623/1.24 |
| 6,451,054 B1 | 9/2002 | Stevens | 623/2.11 |
| 6,454,799 B1 | 9/2002 | Schreck | 623/2.18 |
| 6,461,366 B1 | 10/2002 | Seguin | 606/144 |
| 6,503,272 B2 | 1/2003 | Duerig et al. | 623/1.24 |
| 6,508,833 B2 | 1/2003 | Pavcnik et al. | 623/1.15 |
| 6,564,805 B2 | 5/2003 | Garrison et al. | 128/898 |
| 6,569,196 B1 | 5/2003 | Vesely | 623/2.14 |
| 6,602,286 B1 | 8/2003 | Strecker | 623/1.24 |
| 6,629,534 B1 | 10/2003 | St. Goar et al. | 128/898 |
| 6,635,085 B1 | 10/2003 | Caffey et al. | 623/2.1 |
| 6,666,885 B2 | 12/2003 | Moe | 623/2.12 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |

| Patent | Date | Inventor | Class |
|---|---|---|---|
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,953,332 B1 | 10/2005 | Kurk et al. | 425/275 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |
| 6,964,683 B2 | 11/2005 | Kowalsky et al. | 623/2.36 |
| 6,964,684 B2 | 11/2005 | Ortiz et al. | 623/2.37 |
| 6,966,925 B2 | 11/2005 | Stobie | 623/2.11 |
| 6,966,926 B2 | 11/2005 | Mathis | 623/2.36 |
| 6,974,464 B2 | 12/2005 | Quijano et al. | 606/108 |
| 6,974,474 B2 | 12/2005 | Pavcnik et al. | 623/1.24 |
| 6,974,476 B2 | 12/2005 | McGuckin, Jr. et al. | 623/2.36 |
| 6,976,995 B2 | 12/2005 | Mathis et al. | 623/2.37 |
| 6,979,350 B2 | 12/2005 | Moll et al. | 623/1.24 |
| 6,986,775 B2 | 1/2006 | Morales et al. | 606/139 |
| 6,989,027 B2 | 1/2006 | Allen et al. | 623/2.18 |
| 6,989,028 B2 | 1/2006 | Lashinski et al. | 623/2.37 |
| 6,997,950 B2 | 2/2006 | Chawla | 623/2.1 |
| 6,997,951 B2 | 2/2006 | Solem et al. | 623/2.37 |
| 7,004,176 B2 | 2/2006 | Lau | 128/898 |
| 7,007,396 B2 | 3/2006 | Rudko et al. | 33/512 |
| 7,011,669 B2 | 3/2006 | Kimblad | 606/151 |
| 7,011,681 B2 | 3/2006 | Vesely | 623/2.11 |
| 7,011,682 B2 | 3/2006 | Lashinski et al. | 623/2.37 |
| 7,018,406 B2 | 3/2006 | Seguin et al. | 623/2.1 |
| 7,018,407 B1 | 3/2006 | Wright et al. | 623/2.11 |
| 7,018,408 B2 | 3/2006 | Bailey et al. | 623/2.11 |
| 7,022,134 B1 | 4/2006 | Quijano et al. | 623/1.24 |
| 7,025,780 B2 | 4/2006 | Gabbay | 623/2.18 |
| 7,033,390 B2 | 4/2006 | Johnson et al. | 623/2.11 |
| 7,037,333 B2 | 5/2006 | Myers et al. | 623/2.13 |
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,070,618 B2 | 7/2006 | Streeter | 623/2.36 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 2002/0013571 A1 | 1/2002 | Goldfarb et al. | 606/1 |
| 2002/0026216 A1 | 2/2002 | Grimes | 606/213 |
| 2002/0082630 A1 | 6/2002 | Menz et al. | 606/167 |
| 2002/0123802 A1 | 9/2002 | Snyders | 623/2.18 |
| 2002/0151970 A1 | 10/2002 | Garrison et al. | 623/2.11 |
| 2002/0183835 A1 | 12/2002 | Taylor et al. | 623/2.11 |
| 2002/0183838 A1 | 12/2002 | Liddicoat et al. | 623/2.11 |
| 2002/0198594 A1 | 12/2002 | Schreck | 623/2.11 |
| 2003/0050694 A1 | 3/2003 | Yang et al. | 623/2.11 |
| 2003/0130729 A1 | 7/2003 | Paniagua et al. | 623/2.11 |
| 2003/0163194 A1 | 8/2003 | Quijano et al. | 623/2.11 |
| 2003/0167071 A1 | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138685 A1 | 7/2004 | Clague et al. | |

| | | | | | | | |
|---|---|---|---|---|---|---|---|
| 2004/0138742 A1 | 7/2004 | Myers et al. | 623/2.12 | 2005/0004667 A1 | 1/2005 | Swinford et al. | 623/2.36 |
| 2004/0138743 A1 | 7/2004 | Myers et al. | 623/2.13 | 2005/0010285 A1 | 1/2005 | Lambrecht et al. | 623/2.18 |
| 2004/0138744 A1 | 7/2004 | Lashinski et al. | 623/2.36 | 2005/0010287 A1 | 1/2005 | Macoviak et al. | 623/2.36 |
| 2004/0138745 A1 | 7/2004 | Macoviak et al. | 623/2.36 | 2005/0015112 A1 | 1/2005 | Cohn et al. | 606/200 |
| 2004/0148018 A1 | 7/2004 | Carpentier et al. | 623/2.18 | 2005/0021056 A1 | 1/2005 | St. Goar et al. | 606/144 |
| 2004/0148019 A1 | 7/2004 | Vidlund et al. | 623/2.36 | 2005/0021136 A1 | 1/2005 | Xie et al. | 623/2.14 |
| 2004/0148020 A1 | 7/2004 | Vidlund et al. | 623/2.36 | 2005/0027261 A1 | 2/2005 | Weaver et al. | 604/246 |
| 2004/0153052 A1 | 8/2004 | Mathis | 606/1 | 2005/0027348 A1 | 2/2005 | Case et al. | 623/1.24 |
| 2004/0153146 A1 | 8/2004 | Lashinski et al. | 623/2.36 | 2005/0027351 A1 | 2/2005 | Reuter et al. | 623/2.11 |
| 2004/0153147 A1 | 8/2004 | Mathis | 623/2.37 | 2005/0027353 A1 | 2/2005 | Alferness et al. | 623/2.11 |
| 2004/0158321 A1 | 8/2004 | Reuter et al. | 623/2.36 | 2005/0033398 A1 | 2/2005 | Seguin | 623/1.11 |
| 2004/0162610 A1 | 8/2004 | Liska et al. | 623/2.11 | 2005/0033419 A1 | 2/2005 | Alferness et al. | 623/2.11 |
| 2004/0167539 A1 | 8/2004 | Kuehn et al. | 606/108 | 2005/0033446 A1 | 2/2005 | Deem et al. | 623/23.6 |
| 2004/0167620 A1 | 8/2004 | Ortiz et al. | 623/2.11 | 2005/0038506 A1 | 2/2005 | Webler et al. | 623/2.11 |
| 2004/0172046 A1 | 9/2004 | Hlavka et al. | 606/142 | 2005/0038507 A1 | 2/2005 | Alferness et al. | 623/2.11 |
| 2004/0176839 A1 | 9/2004 | Huynh et al. | 623/2.4 | 2005/0043790 A1 | 2/2005 | Seguin | 623/2.18 |
| 2004/0176840 A1 | 9/2004 | Langberg et al. | 623/2.37 | 2005/0043792 A1 | 2/2005 | Solem et al. | 623/2.36 |
| 2004/0181238 A1 | 9/2004 | Zarbatany et al. | 606/108 | 2005/0049679 A1 | 3/2005 | Taylor et al. | 623/1.15 |
| 2004/0186444 A1 | 9/2004 | Daly et al. | 604/247 | 2005/0049692 A1 | 3/2005 | Numamoto et al. | 623/1.24 |
| 2004/0186558 A1 | 9/2004 | Pavcnik et al. | 623/1.24 | 2005/0049696 A1 | 3/2005 | Siess et al. | 623/2.11 |
| 2004/0186561 A1 | 9/2004 | McGuckin, Jr. et al. | 623/1.36 | 2005/0049697 A1 | 3/2005 | Sievers | 623/2.26 |
| 2004/0186563 A1 | 9/2004 | Lobbi | 623/2.11 | 2005/0054977 A1 | 3/2005 | Laird et al. | 604/96.01 |
| 2004/0186565 A1 | 9/2004 | Schreck | 623/2.18 | 2005/0055079 A1 | 3/2005 | Duran | 623/1.13 |
| 2004/0186566 A1 | 9/2004 | Hindrichs et al. | 623/2.37 | 2005/0055087 A1 | 3/2005 | Starksen | 623/2.11 |
| 2004/0193191 A1 | 9/2004 | Starksen et al. | 606/153 | 2005/0055088 A1* | 3/2005 | Liddicoat et al. | 623/2.11 |
| 2004/0193253 A1 | 9/2004 | Thorpe et al. | 623/1.24 | 2005/0055089 A1 | 3/2005 | Macoviak et al. | 623/2.37 |
| 2004/0193260 A1 | 9/2004 | Alferness et al. | 623/2.11 | 2005/0060029 A1 | 3/2005 | Le et al. | 623/2.11 |
| 2004/0199155 A1 | 10/2004 | Mollenauer | 606/27 | 2005/0060030 A1 | 3/2005 | Lashinski et al. | 623/2.37 |
| 2004/0199183 A1 | 10/2004 | Oz et al. | 606/142 | 2005/0065460 A1 | 3/2005 | Laird | 604/20 |
| 2004/0199191 A1 | 10/2004 | Schwartz | 606/159 | 2005/0065550 A1 | 3/2005 | Starksen et al. | 606/219 |
| 2004/0204758 A1 | 10/2004 | Eberhardt et al. | 623/2.15 | 2005/0065594 A1 | 3/2005 | DiMatteo et al. | 623/1.24 |
| 2004/0206363 A1 | 10/2004 | McCarthy et al. | 128/898 | 2005/0065597 A1 | 3/2005 | Lansac | 623/2.11 |
| 2004/0210240 A1 | 10/2004 | Saint | 606/139 | 2005/0070998 A1 | 3/2005 | Rourke et al. | 623/2.11 |
| 2004/0210301 A1 | 10/2004 | Obermiller | 623/1.24 | 2005/0075584 A1 | 4/2005 | Cali | 600/587 |
| 2004/0210303 A1 | 10/2004 | Sedransk | 623/2.1 | 2005/0075659 A1 | 4/2005 | Realyvasquez et al. | 606/167 |
| 2004/0210304 A1* | 10/2004 | Seguin et al. | 623/2.11 | 2005/0075662 A1 | 4/2005 | Pedersen et al. | 606/194 |
| 2004/0210305 A1 | 10/2004 | Shu et al. | 623/2.11 | 2005/0075712 A1 | 4/2005 | Biancucci et al. | 623/1.11 |
| 2004/0210306 A1 | 10/2004 | Quijano et al. | 623/2.17 | 2005/0075713 A1 | 4/2005 | Biancucci et al. | 623/1.11 |
| 2004/0210307 A1 | 10/2004 | Khairkhahan | 623/2.18 | 2005/0075717 A1 | 4/2005 | Nguyen et al. | 623/1.26 |
| 2004/0215333 A1 | 10/2004 | Duran et al. | 623/1.24 | 2005/0075718 A1 | 4/2005 | Nguyen et al. | 623/1.26 |
| 2004/0215339 A1 | 10/2004 | Drasler et al. | 623/3.1 | 2005/0075719 A1 | 4/2005 | Bergheim | 623/1.26 |
| 2004/0220654 A1 | 11/2004 | Mathis et al. | 623/1.11 | 2005/0075720 A1 | 4/2005 | Nguyen et al. | 623/1.26 |
| 2004/0220657 A1 | 11/2004 | Nieminen et al. | 623/1.15 | 2005/0075723 A1 | 4/2005 | Schroeder et al. | 623/2.1 |
| 2004/0225322 A1 | 11/2004 | Garrison et al. | 606/200 | 2005/0075724 A1 | 4/2005 | Svanidze et al. | 623/2.11 |
| 2004/0225344 A1 | 11/2004 | Hoffa et al. | 623/1.1 | 2005/0075725 A1 | 4/2005 | Rowe | 623/2.14 |
| 2004/0225348 A1 | 11/2004 | Case et al. | 623/1.15 | 2005/0075726 A1 | 4/2005 | Svanidze et al. | 623/2.14 |
| 2004/0225352 A1 | 11/2004 | Osborne et al. | 623/1.24 | 2005/0075728 A1 | 4/2005 | Nguyen et al. | 623/2.17 |
| 2004/0225353 A1 | 11/2004 | McGuckin, Jr. et al. | 623/2.11 | 2005/0075729 A1 | 4/2005 | Nguyen et al. | 623/2.18 |
| 2004/0225354 A1 | 11/2004 | Allen et al. | 623/2.11 | 2005/0075730 A1 | 4/2005 | Myers et al. | 623/2.18 |
| 2004/0225355 A1 | 11/2004 | Stevens | 623/2.11 | 2005/0075731 A1 | 4/2005 | Artof et al. | 623/2.18 |
| 2004/0225356 A1 | 11/2004 | Frater | 623/2.14 | 2005/0080483 A1 | 4/2005 | Solem et al. | 623/2.11 |
| 2004/0230117 A1 | 11/2004 | Tosaya et al. | 600/439 | 2005/0085900 A1 | 4/2005 | Case et al. | 623/1.24 |
| 2004/0230297 A1 | 11/2004 | Thornton | 623/1.24 | 2005/0085903 A1 | 4/2005 | Lau | 623/2.11 |
| 2004/0236411 A1 | 11/2004 | Sarac et al. | 623/1.26 | 2005/0085904 A1 | 4/2005 | Lemmon | 623/2.11 |
| 2004/0236418 A1 | 11/2004 | Stevens | 623/2.11 | 2005/0090846 A1 | 4/2005 | Pedersen et al. | 606/159 |
| 2004/0236419 A1 | 11/2004 | Milo | 623/2.36 | 2005/0096735 A1 | 5/2005 | Hojeibane et al. | 623/1.24 |
| 2004/0243153 A1 | 12/2004 | Liddicoat et al. | 606/151 | 2005/0096738 A1 | 5/2005 | Cali et al. | 623/2.18 |
| 2004/0243219 A1 | 12/2004 | Fischer et al. | 623/1.15 | 2005/0096739 A1 | 5/2005 | Cao | 623/2.19 |
| 2004/0243227 A1 | 12/2004 | Starksen et al. | 623/2.11 | 2005/0096740 A1 | 5/2005 | Langberg et al. | 623/2.36 |
| 2004/0243228 A1 | 12/2004 | Kowalsky et al. | 623/2.11 | 2005/0101975 A1 | 5/2005 | Nguyen et al. | 606/151 |
| 2004/0243230 A1 | 12/2004 | Navia et al. | 623/2.36 | 2005/0102026 A1 | 5/2005 | Turner et al. | 623/2.1 |
| 2004/0249452 A1 | 12/2004 | Adams et al. | 623/2.36 | 2005/0107810 A1 | 5/2005 | Morales et al. | 606/143 |
| 2004/0254600 A1 | 12/2004 | Zarbatany et al. | 606/194 | 2005/0107811 A1 | 5/2005 | Starksen et al. | 606/143 |
| 2004/0254636 A1 | 12/2004 | Flagle et al. | 623/1.24 | 2005/0107812 A1 | 5/2005 | Starksen et al. | 606/143 |
| 2004/0260276 A1 | 12/2004 | Rudko et al. | 606/15 | 2005/0107872 A1 | 5/2005 | Mensah et al. | 623/2.14 |
| 2004/0260317 A1 | 12/2004 | Bloom et al. | 606/151 | 2005/0113910 A1 | 5/2005 | Paniagua et al. | 623/2.14 |
| 2004/0260322 A1 | 12/2004 | Rudko et al. | 606/167 | 2005/0119673 A1 | 6/2005 | Gordon et al. | 606/151 |
| 2004/0260389 A1 | 12/2004 | Case et al. | 623/1.24 | 2005/0119734 A1 | 6/2005 | Spence et al. | 623/2.11 |
| 2004/0260390 A1 | 12/2004 | Sarac et al. | 623/1.24 | 2005/0119735 A1 | 6/2005 | Spence et al. | 623/2.36 |
| 2004/0260393 A1 | 12/2004 | Rahdert et al. | 623/2.36 | 2005/0125011 A1 | 6/2005 | Spence et al. | 606/144 |
| 2004/0260394 A1 | 12/2004 | Douk et al. | 623/2.36 | 2005/0131438 A1 | 6/2005 | Cohn | 606/170 |
| 2004/0267357 A1 | 12/2004 | Allen et al. | 623/2.11 | 2005/0137449 A1 | 6/2005 | Nieminen et al. | 600/37 |
| 2005/0004583 A1 | 1/2005 | Oz et al. | 606/142 | 2005/0137450 A1 | 6/2005 | Aronson et al. | 600/37 |

| Publication No. | Date | Inventor | Class |
|---|---|---|---|
| 2005/0137451 A1 | 6/2005 | Gordon et al. | 600/37 |
| 2005/0137676 A1 | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1 | 6/2005 | Salahieh et al. | 623/2.11 |
| 2005/0137688 A1 | 6/2005 | Salahieh et al. | 623/2.11 |
| 2005/0137689 A1 | 6/2005 | Salahieh et al. | 623/2.11 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |
| 2005/0137694 A1 | 6/2005 | Haug et al. | 623/2.11 |
| 2005/0137696 A1 | 6/2005 | Salahieh et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1* | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Starksen et al. | 604/510 |
| 2006/0025784 A1 | 2/2006 | Starksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1* | 4/2006 | Huber | 623/2.1 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |

| | | | | | |
|---|---|---|---|---|---|
| 2006/0106278 A1 | 5/2006 | Machold et al. ............... 600/37 | WO | WO 2004/045370 | 6/2004 |
| 2006/0106279 A1 | 5/2006 | Machold et al. ............... 600/37 | WO | WO 2004/045378 | 6/2004 |
| 2006/0106456 A9 | 5/2006 | Machold et al. ............. 623/2.36 | WO | WO 2004/045463 | 6/2004 |
| 2006/0111660 A1 | 5/2006 | Wolf et al. ...................... 604/9 | WO | WO 2004/047677 | 6/2004 |
| 2006/0111773 A1 | 5/2006 | Rittgers et al. ............. 623/1.24 | WO | WO 2004/060217 | 7/2004 |
| 2006/0111774 A1 | 5/2006 | Samkov et al. ............. 623/2.25 | WO | WO 2004/060470 | 7/2004 |
| 2006/0116572 A1 | 6/2006 | Case ............................ 600/424 | WO | WO 2004/062725 | 7/2004 |
| 2006/0116756 A1 | 6/2006 | Solem et al. ............... 623/2.11 | WO | WO 2004/066803 | 8/2004 |
| 2006/0122686 A1 | 6/2006 | Gilad et al. ................ 623/1.13 | WO | WO 2004/066826 | 8/2004 |
| 2006/0122692 A1 | 6/2006 | Gilad et al. ................ 623/1.24 | WO | WO 2004/069287 | 8/2004 |
| 2006/0122693 A1 | 6/2006 | Biadillah et al. ........... 623/1.24 | WO | WO 2004/075789 | 9/2004 |
| 2006/0127443 A1 | 6/2006 | Helmus ....................... 424/423 | WO | WO 2004/080352 | 9/2004 |
| 2006/0129235 A1 | 6/2006 | Seguin et al. .............. 623/2.11 | WO | WO 2004/082523 | 9/2004 |
| 2006/0129236 A1 | 6/2006 | McCarthy .................. 623/2.36 | WO | WO 2004/082527 | 9/2004 |
| 2006/0135476 A1 | 6/2006 | Kutryk et al. ................... 514/59 | WO | WO 2004/082528 | 9/2004 |
| 2006/0135964 A1 | 6/2006 | Vesely ........................ 606/108 | WO | WO 2004/082536 | 9/2004 |
| 2006/0135967 A1 | 6/2006 | Realyvasquez ............. 606/142 | WO | WO 2004/082537 | 9/2004 |
| 2006/0136044 A1 | 6/2006 | Osborne ..................... 623/1.24 | WO | WO 2004/082538 | 9/2004 |
| 2006/0136045 A1 | 6/2006 | Flagle et al. ............... 623/1.24 | WO | WO 2004/082757 | 9/2004 |
| 2006/0136052 A1 | 6/2006 | Vesely ........................ 623/2.18 | WO | WO 2004/084746 | 10/2004 |
| 2006/0136054 A1 | 6/2006 | Berg et al. .................. 623/2.38 | WO | WO 2004/084770 | 10/2004 |
| 2006/0142846 A1 | 6/2006 | Pavcnik et al. ............. 623/1.24 | WO | WO 2004/089246 | 10/2004 |
| 2006/0142847 A1 | 6/2006 | Shaknovich ................ 623/1.24 | WO | WO 2004/089250 | 10/2004 |
| 2006/0142848 A1 | 6/2006 | Gabbay ....................... 623/1.26 | WO | WO 2004/089253 | 10/2004 |
| 2006/0142854 A1 | 6/2006 | Alferness et al. ........... 623/2.11 | WO | WO 2004/091449 | 10/2004 |
| 2006/0149358 A1 | 7/2006 | Zilla et al. .................. 623/1.22 | WO | WO 2004/091454 | 10/2004 |
| 2006/0149360 A1 | 7/2006 | Schwammenthal et al.  623/1.24 | WO | WO 2004/093638 | 11/2004 |
| 2006/0149367 A1 | 7/2006 | Sieracki ...................... 623/2.21 | WO | WO 2004/093726 | 11/2004 |
| 2006/0149368 A1 | 7/2006 | Spence ....................... 623/2.37 | WO | WO 2004/093728 | 11/2004 |
| 2006/0161133 A1 | 7/2006 | Laird et al. ................. 604/509 | WO | WO 2004/093730 | 11/2004 |
| 2006/0161248 A1 | 7/2006 | Case et al. ..................... 623/2.1 | WO | WO 2004/093745 | 11/2004 |
| 2006/0161249 A1 | 7/2006 | Realyvasquez et al. .... 623/2.11 | WO | WO 2004/093935 | 11/2004 |
| 2006/0161250 A1 | 7/2006 | Shaw .......................... 623/2.17 | WO | WO 2004/096100 | 11/2004 |
| 2006/0167468 A1 | 7/2006 | Gabbay ....................... 606/108 | WO | WO 2004/103222 | 12/2004 |
| 2006/0167541 A1 | 7/2006 | Lattouf ....................... 623/2.11 | WO | WO 2004/103223 | 12/2004 |
| 2006/0167542 A1 | 7/2006 | Quintessenza .............. 623/2.12 | WO | WO 2004/105584 | 12/2004 |
| 2006/0167543 A1 | 7/2006 | Bailey et al. ............... 623/2.18 | WO | WO 2004/105651 | 12/2004 |
| 2006/0173490 A1* | 8/2006 | Lafontaine et al. .......... 606/200 | WO | WO 2004/112582 | 12/2004 |
| 2007/0032850 A1* | 2/2007 | Ruiz et al. .................. 623/1.11 | WO | WO 2004/112585 | 12/2004 |
| 2007/0162103 A1* | 7/2007 | Case et al. .................. 623/1.13 | WO | WO 2004/112643 | 12/2004 |
| | | | WO | WO 2004/112652 | 12/2004 |
| | FOREIGN PATENT DOCUMENTS | | WO | WO 2004/112657 | 12/2004 |
| | | | WO | WO 2004/112658 | 12/2004 |
| EP | 0 380 666 | 8/1990 | WO | WO 2005/000152 | 1/2005 |
| EP | 0 466 518 | 1/1992 | WO | WO 2005/002424 | 1/2005 |
| FR | 2 728 457 | 6/1996 | WO | WO 2005/002466 | 1/2005 |
| WO | WO 88/00459 | 1/1988 | WO | WO 2005/004753 | 1/2005 |
| WO | WO 90/15582 | 12/1990 | WO | WO 2005/007017 | 1/2005 |
| WO | WO 94/04081 | 3/1994 | WO | WO 2005/007018 | 1/2005 |
| WO | WO 95/01669 | 1/1995 | WO | WO 2005/007036 | 1/2005 |
| WO | WO 96/19159 | 6/1996 | WO | WO 2005/007037 | 1/2005 |
| WO | WO 98/03656 | 1/1998 | WO | WO 2005/009285 | 2/2005 |
| WO | WO 98/46115 | 10/1998 | WO | WO 2005/009286 | 2/2005 |
| WO | WO 99/04724 | 2/1999 | WO | WO 2005/009505 | 2/2005 |
| WO | WO 00/67679 | 11/2000 | WO | WO 2005/009506 | 2/2005 |
| WO | WO 01/15650 | 3/2001 | WO | WO 2005/011473 | 2/2005 |
| WO | WO 01/17462 | 3/2001 | WO | WO 2005/011534 | 2/2005 |
| WO | WO 03/047468 | 6/2003 | WO | WO 2005/011535 | 2/2005 |
| WO | WO 03/084443 | 10/2003 | WO | WO 2005/013860 | 2/2005 |
| WO | WO 2004/019825 | 3/2004 | WO | WO 2005/018507 | 3/2005 |
| WO | WO 2004/021893 | 3/2004 | WO | WO 2005/021063 | 3/2005 |
| WO | WO 2004/023980 | 3/2004 | WO | WO 2005/023155 | 3/2005 |
| WO | WO 2004/030568 | 4/2004 | WO | WO 2005/025644 | 3/2005 |
| WO | WO 2004/030569 | 4/2004 | WO | WO 2005/027790 | 3/2005 |
| WO | WO 2004/030570 | 4/2004 | WO | WO 2005/027797 | 3/2005 |
| WO | WO 2004/032724 | 4/2004 | WO | WO 2005/034812 | 4/2005 |
| WO | WO 2004/032796 | 4/2004 | WO | WO 2005/039428 | 5/2005 |
| WO | WO 2004/037128 | 5/2004 | WO | WO 2005/039452 | 5/2005 |
| WO | WO 2004/037317 | 5/2004 | WO | WO 2005/046488 | 5/2005 |
| WO | WO 2004/039432 | 5/2004 | WO | WO 2005/046528 | 5/2005 |
| WO | WO 2004/043265 | 5/2004 | WO | WO 2005/046529 | 5/2005 |
| WO | WO 2004/043273 | 5/2004 | WO | WO 2005/046530 | 5/2005 |
| WO | WO 2004/043293 | 5/2004 | WO | WO 2005/046531 | 5/2005 |

| | | |
|---|---|---|
| WO | WO 2005/048883 | 6/2005 |
| WO | WO 2005/049103 | 6/2005 |
| WO | WO 2005/051226 | 6/2005 |
| WO | WO 2005/055811 | 6/2005 |
| WO | WO 2005/055883 | 6/2005 |
| WO | WO 2005/058206 | 6/2005 |
| WO | WO 2005/065585 | 7/2005 |
| WO | WO 2005/065593 | 7/2005 |
| WO | WO 2005/065594 | 7/2005 |
| WO | WO 2005/070342 | 8/2005 |
| WO | WO 2005/070343 | 8/2005 |
| WO | WO 2005/072654 | 8/2005 |
| WO | WO 2005/072655 | 8/2005 |
| WO | WO 2005/079706 | 9/2005 |
| WO | WO 2005/082288 | 9/2005 |
| WO | WO 2005/082289 | 9/2005 |
| WO | WO 2005/084595 | 9/2005 |
| WO | WO 2005/087139 | 9/2005 |
| WO | WO 2005/087140 | 9/2005 |
| WO | WO 2006/000763 | 1/2006 |
| WO | WO 2006/000776 | 1/2006 |
| WO | WO 2006/002492 | 1/2006 |
| WO | WO 2006/004679 | 1/2006 |
| WO | WO 2006/005015 | 1/2006 |
| WO | WO 2006/009690 | 1/2006 |
| WO | WO 2006/011127 | 2/2006 |
| WO | WO 2006/012011 | 2/2006 |
| WO | WO 2006/012013 | 2/2006 |
| WO | WO 2006/012038 | 2/2006 |
| WO | WO 2006/012068 | 2/2006 |
| WO | WO 2006/012322 | 2/2006 |
| WO | WO 2006/019498 | 2/2006 |
| WO | WO 2006/026371 | 3/2006 |
| WO | WO 2006/026377 | 3/2006 |
| WO | WO 2006/026912 | 3/2006 |
| WO | WO 2006/027499 | 3/2006 |
| WO | WO 2006/028821 | 3/2006 |
| WO | WO 2006/029062 | 3/2006 |
| WO | WO 2006/031436 | 3/2006 |
| WO | WO 2006/031469 | 3/2006 |
| WO | WO 2006/032051 | 3/2006 |
| WO | WO 2006/034245 | 3/2006 |
| WO | WO 2006/035415 | 4/2006 |
| WO | WO 2006/041505 | 4/2006 |
| WO | WO 2006/044679 | 4/2006 |
| WO | WO 2006/048664 | 5/2006 |
| WO | WO 2006/050459 | 5/2006 |
| WO | WO 2006/050460 | 5/2006 |
| WO | WO 2006/054107 | 5/2006 |
| WO | WO 2006/054930 | 5/2006 |
| WO | WO 2006/055982 | 5/2006 |
| WO | WO 2006/060546 | 6/2006 |
| WO | WO 2006/063108 | 6/2006 |
| WO | WO 2006/063181 | 6/2006 |
| WO | WO 2006/063199 | 6/2006 |
| WO | WO 2006/064490 | 6/2006 |
| WO | WO 2006/065212 | 6/2006 |
| WO | WO 2006/065930 | 6/2006 |
| WO | WO 2006/066148 | 6/2006 |
| WO | WO 2006/066150 | 6/2006 |
| WO | WO 2006/069094 | 6/2006 |
| WO | WO 2006/070372 | 7/2006 |
| WO | WO 2006/073628 | 7/2006 |
| WO | WO 2006/076890 | 7/2006 |

OTHER PUBLICATIONS

US 6,723,117, 04/2004, Menz et al. (withdrawn)

* cited by examiner

VASCULAR CATHETER, SYSTEM, AND METHOD

FIELD OF THE INVENTION

The present invention relates generally to catheters, systems, and methods for use in a lumen; and more particularly to catheters, systems, and methods useful in a lumen of the cardiovasculature system.

BACKGROUND OF THE INVENTION

Diseases of the heart valves are grouped according to which valve(s) are involved and the amount of blood flow that is disrupted. The most common valve problems occur in the mitral and aortic valves. Diseases of the tricuspid and pulmonary valves are fairly rare.

The aortic valve regulates the blood flow from the heart's left ventricle into the aorta. The aorta is the main vessel that supplies oxygenated blood to the rest of the body. Diseases of the aorta can have a significant impact on an individual. Examples of such diseases include aortic regurgitation and aortic stenosis.

Aortic regurgitation is also called aortic insufficiency or aortic incompetence. It is a condition in which blood flows backward from a widened or weakened aortic valve into the left ventricle of the heart. In its most serious form, aortic regurgitation is caused by an infection that leaves holes in the valve leaflets. Symptoms of aortic regurgitation may not appear for years. When symptoms do appear, it is because the left ventricle must work harder as compared to an uncompromised ventricle to make up for the backflow of blood. The ventricle eventually gets larger and fluid backs up.

Aortic stenosis is a narrowing or blockage of the aortic valve. Aortic stenosis occurs when the valve leaflets of the aorta become coated with deposits. The deposits change the shape of the leaflets and reduce blood flow through the valve. The left ventricle has to work harder as compared to an uncompromised ventricle to make up for the reduced blood flow. Over time, the extra work can weaken the heart muscle.

DETAILED DESCRIPTION

Figure 1:
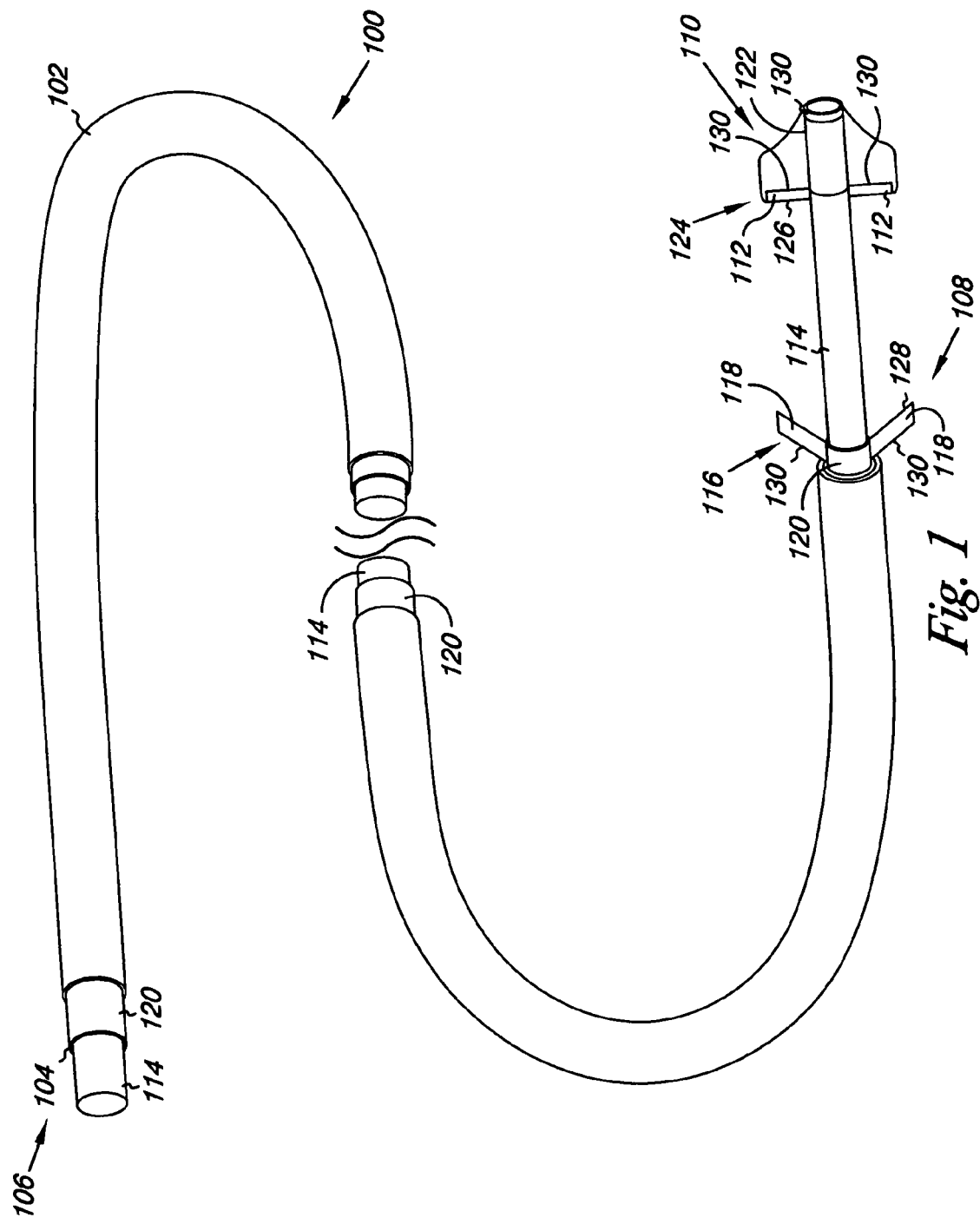
FIG. 1 illustrates an embodiment of a catheter in perspective view having partial sectional views to show detail.

Embodiments of the present invention are directed to catheters, systems, and methods for valve repair, replacement and/or augmentation using a minimally-invasive technique. Embodiments of the present invention include an apparatus having a catheter that includes cutting heads for preparing cardiac tissue to receive a cardiac valve. Embodiments of the apparatus can further include an expandable stent positioned over at least a portion of an inflatable balloon on the catheter, where the expandable stent can be deployed over cardiac tissue sheared with the cutting heads.

In an additional embodiment, the catheter can further include the cardiac valve and an expandable filter positioned within a sheath, where retracting the sheath deploys the cardiac valve and at least a portion of the expandable filter proximal the inflatable balloon and the expandable stent. The embodiments of the present invention can, in one example, be used during valve replacement in individuals having heart valve disease.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of valve. In addition, the elements shown in the various embodiments are not necessarily to scale.

The Figures presented herein provided illustrations of non-limiting embodiments of the present invention. For example, FIG. 1 provides an illustration of a catheter 100. Catheter 100 includes an elongate body 102 having a first lumen 104 extending between a proximal end 106 and a distal end 108 of the elongate body 102. In one embodiment, the first lumen 104 allows for additional elongate members to travel along a longitudinal axis of the elongate body 102.

The catheter 100 further includes a first cutting head 110 having a blade 112 and an elongate pulling member 114. The first cutting head 110 can be positioned proximal the distal end 108 of the elongate body 102 with the elongate pulling member 114 extending through the first lumen 104. In one embodiment, the elongate pulling member 114 can slide within the first lumen 104 to move the first cutting head 110 relative the distal end 108 of the elongate body 102.

The catheter 100 also includes a second cutting head 116 having a blade 118. The second cutting head 116 can be positioned adjacent the distal end 108 of the elongate body 102 between the distal end 108 and the first cutting head 110. The blade 112 of the first cutting head 110 can move relative the blade 118 of the second cutting head 116 to provide a shearing action. In one example, the shearing action can be sufficient for cutting cardiac tissue.

FIG. 1 further illustrates an embodiment in which the second cutting head includes an elongate pushing member 120. In one embodiment, the elongate pushing member 120 can slide within the first lumen 104 to move the second cutting head 116 relative the distal end 108 of the elongate body 102 and the first cutting head 110. In one embodiment, the elongate pulling member 120 can be arranged concentrically with the elongate pushing member 114 in the first lumen 104.

As illustrated, the elongate pulling member 114, the elongate push member 120 and the first lumen 104 of the elongate body 102 can be positioned coaxially. In one embodiment, the lumen 104 has a diameter sufficient to accommodate the elongate push member 120. Similarly, the elongate push member 120 had a diameter sufficient to accommodate the elongate pulling member 114.

In addition, the elongate pulling member 114 and the elongate push member 120 can be structured such that their relative rotational movement is restricted. In other words, relative axial rotation of the elongate pulling member 114 and the elongate push member 120 is restricted due to the structure of the members 114 and 120. For example, this can be accomplished using one or more physical structures formed in and/or attached to the members 114 and 120. In one embodiment, one of the members 114 or 120 can include a channel through which an extension from the other of the members 114 or 120 can travel so as to inhibit axial rotation of the members 114 and 120. Alternatively, the members 114 and 120 could have a cross-sectional shape that inhibits relative axial rotation. Examples of such cross-sectional shapes include oval or elliptical cross-sectional shapes. Other shapes are also possible.

In addition to providing a sufficient diameter, a gap can exist between the opposing surfaces of the first lumen 104 and the elongate push member 120 to allow the elongate push member 120 to move through the first lumen 104 from force applied at the proximal end of the elongate push member 120. Similarly, a gap can exist between the opposing surfaces of the elongate push member 120 and the elongate pulling member 114 to allow the elongate push member 120 and the elongate pulling member 114 to move relative each other from force applied at the proximal end of the elongate push member 120 and/or the elongate pulling member 114. The elongate pull member 114 can further include a lumen for tracking over a guidewire. A lubricant can be included on the surfaces of the elongate pulling member 114, the elongate push member 120 and the first lumen 104.

The first cutting head 110 further includes a shape conducive to passing the catheter 100 to pass through a lumen (e.g., a lumen of the cardiovascular system). For example, the first cutting head 110 can include a conical shape having a first end 122 and a second end 124, where the first end 122 has a diameter that is less than a diameter of the second end 124. Other shapes are also possible. In addition, the shape of the first cutting head 110 can be configured to protectively house the blade 112 from structures passing by the first end 122 towards the second end 124. In other words, the shape of the first cutting head 110 can be used to shield the blade 112 from unintentionally interfering and/or cutting tissue within a lumen.

In one embodiment, the blade 112 can be radially positioned relative the elongate pulling member 114 generally along the second end 124 of the first cutting head 110. As will be appreciated, the first cutting head 110 can include more than one blade 112 as illustrated in FIG. 1. Each blade 112 and 118 further includes a cutting edge 126 and 128, respectively, in alignment so as to provide shearing action between a pair of the cutting edges 126 and 128 of the blades 112 and 118. For example, the first cutting head 110 can move relative the second cutting head 116 to allow the cutting edge 126 of the blade 112 of the first cutting head 110 to slide past the cutting edge 128 of the blade 116 of the second cutting head 116. Example of suitable materials for the blades 112 and 118 include, but are not limited to, stainless steel (e.g., 316L) and titanium.

In one embodiment, blades 112 and 118 can be secured to the first cutting head 110 and the second cutting head 116, respectively, in any number of ways. For example, blades 112 and 118 can be secured to the cutting heads 110 and 112 through the use of mechanical fasteners, such as screws, and/or interlocking pins and sockets. In addition, blades 112 and 118 can be secured to the cutting heads 110 and 112 through the use of chemical adhesives. Examples of such chemical adhesives include, but are not limited to, medical grade adhesives such as cyanoacrylate, acrylic, silicone, and urethane adhesives.

In an additional embodiment, the first cutting head 110 can be configured to receive and house at least a portion of the second cutting head 116, including the blade 118, such that the second blade 118 does not pass beyond the first cutting head 110. For example, the first cutting head can include a socket that extends radially relative the elongate pulling member 114 and distally from the blade 112 to receive the blade 118 of the second cutting head 116 as the blade 118 passes the blade 112. In one embodiment, the blade 118 can be positioned within the socket of the first cutting head 110 as the catheter 100 is moved through a lumen.

Catheter 100 can have various lengths between the proximal end 106 and the first cutting head 110. In one embodiment, the length between the proximal end 106 and the first cutting head 110 would be sufficient to allow the catheter 100 to be percutaneously implanted through a patient's vasculature to position the cutting heads (e.g., the first and second cutting heads) at a predetermined location. Examples of the predetermined locations include, but are not limited to, cardiovascular locations such as on or adjacent to a cardiac valve of the heart (e.g., the aortic valve), including within a chamber of the patient's heart (e.g., the left ventricle of the heart). As will be appreciated, the length between the proximal end 106 and the first cutting head 110 will be dependent upon each patient's physiological structure and the predetermined location within the patient. By way of example only, the length between the proximal end 106 and the first cutting head 110 could be up to, and including, approximately 100 cm. Lengths greater than 100 cm are also possible.

The elongate body 102, the elongate pulling member 114, the elongate pushing member 120, the second cutting head 116 and the first cutting head 110 can be formed from a wide variety of materials and in a wide variety of configurations. For example, the materials may include, but are not limited to, one or more of polyvinyl chloride (PVC), polyethylene (PE), polyolefin copolymer (POC), polyethylene terephthalate (PET), polyamid, mixtures, and block co-polymers thereof. Alternatively, the materials may include one or more alloys in any number of configurations. For example, the materials may include stainless steel (e.g., 316L), titanium, or other medical grade alloys as are known. These materials may also have a woven configuration or a solid extruded configuration.

The selection of material and configuration allows for the elongate body 102, the elongate pulling member 114, the elongate pushing member 120, the second cutting head 116 and the first cutting head 110 to each have the flexibility, and the ability to be either pushed and/or pulled thereby accomplishing the actions described for the components herein. As will be appreciated, selection of the material can be based generally on a broad range of technical properties, including, but not limited to, modulus of elasticity, flexural modulus, and Shore A hardness required for the embodiments of the present invention. Components of the present apparatus and/or system can also be coated for lubrication, for abrasion resistance, or to deliver an anticoagulatory drug.

In an additional embodiment, the catheter 100 can further include radiopaque markers 130. For example, radiopaque markers (e.g., attached or coated) can be used to mark the location of the first cutting head 110 and the second cutting head 116. In addition, radiopaque markers can be used to mark the location of blades 112 and 118. Other portions of catheter 100 can also be marked with radiopaque markers as necessary to allow for visualization of the location and position of parts of the catheter 100. Examples of radiopaque material include, but are not limited to, gold, tantalum, and platinum.

Figure 2:
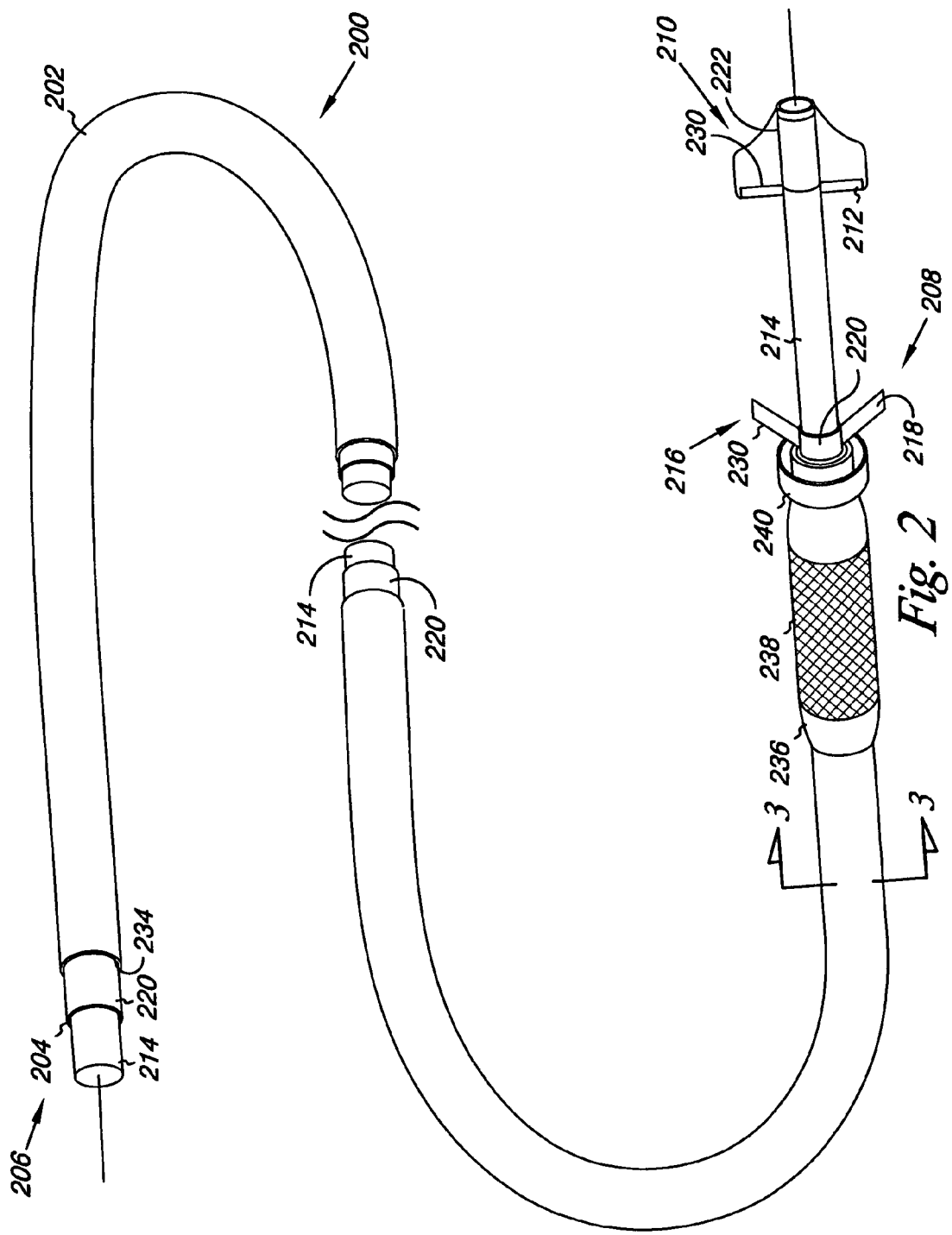
FIG. 2 illustrates an embodiment of a catheter in perspective view having partial sectional views to show detail.

FIG. 2 provides an illustration of a catheter 200 according to an additional embodiment of the present invention. Catheter 200 includes elongate body 202 having the first lumen 204 extending between the proximal end 206 and the distal end 208 of the elongate body 202. In addition, catheter 200 includes the first cutting head 210 and the second cutting head 216 as described herein.

In addition to the structures described herein, the elongate body 202 of catheter 200 further includes a second lumen 234. In one embodiment, the second lumen 234 can extend between the proximal end 206 and the distal end 208 of the elongate body 202, where the second lumen 234 can be coupled in fluid tight communication to an inflatable balloon 236 on the elongate body 202.

In one embodiment, the inflatable balloon 236 can be positioned adjacent the distal end 208 of the elongate body 202 and proximal to the second cutting head 216. The inflatable balloon 236 can be inflated from a deflated state to an inflated state by pressure applied by fluid moving through the second lumen 234. In addition, the catheter 200 further includes an expandable stent 238 positioned over at least a portion of the inflatable balloon 236. The expandable stent 238 can move between a compressed state, as shown in FIG. 2, and an expanded state using the inflatable balloon 236. In one embodiment, the expandable stent 238 can be deployed over cardiac tissue sheared using the first and second cutting heads 210 and 216 using the inflatable balloon 236.

Catheter 200 can further include an annular push ring 240 positioned between the second cutting head 216 and the inflatable balloon 236. The annular push ring 240 can be used for contacting and moving at least a portion of cardiac tissue sheared with the first and second cutting heads 210 and 216. For example, the first and second cutting heads 210 and 216 can be used to shear cardiac tissue (e.g., one or more cusps of a valve). The annular push ring 240 can then be advanced into contact with the sheared cardiac tissue. As the annular push ring 240 advances the sheared cardiac tissue can be directed towards the wall of the lumen. Stent 238 can then be positioned over at least a portion of the sheared cardiac tissue positioned using the annular push ring 240. Stent 238 can then be deployed using the inflatable balloon 236 to position at least a portion of the sheared cardiac tissue between the expanded stent 238 and the wall of the lumen. As will be appreciated, the dimensions and physical characteristics of the stent 238 will be dependent upon the location in which the stent 238 is to be implanted.

In an additional embodiment, the annular push ring 240 can be radially expandable. For example, the annular push ring 240 can be configured as an expandable balloon in fluid tight communication with the second lumen 234. In one embodiment, the fluid pressure necessary to inflate the annular push ring 240 in its expandable balloon configuration is less than that necessary to inflate the inflatable balloon 236. In this way, a lesser fluid pressure applied through the second lumen 234 can be used to first inflate the annular push ring 240, with additional fluid pressure applied through the second lumen 234 then used to inflate the inflatable balloon 236 to deploy the expanded stent 238 as discussed. In an alternative embodiment, a separate fluid lumen could be coupled in fluid communication with the expandable annular push ring 240. As will be appreciated, the annular push ring 240 can be formed of any number of suitable materials (e.g., metal, polymer, and composite), including those provided herein. In addition, other configurations for allowing the annular push ring 240 to expand (e.g., radially expand) are also possible.

Figure 3:
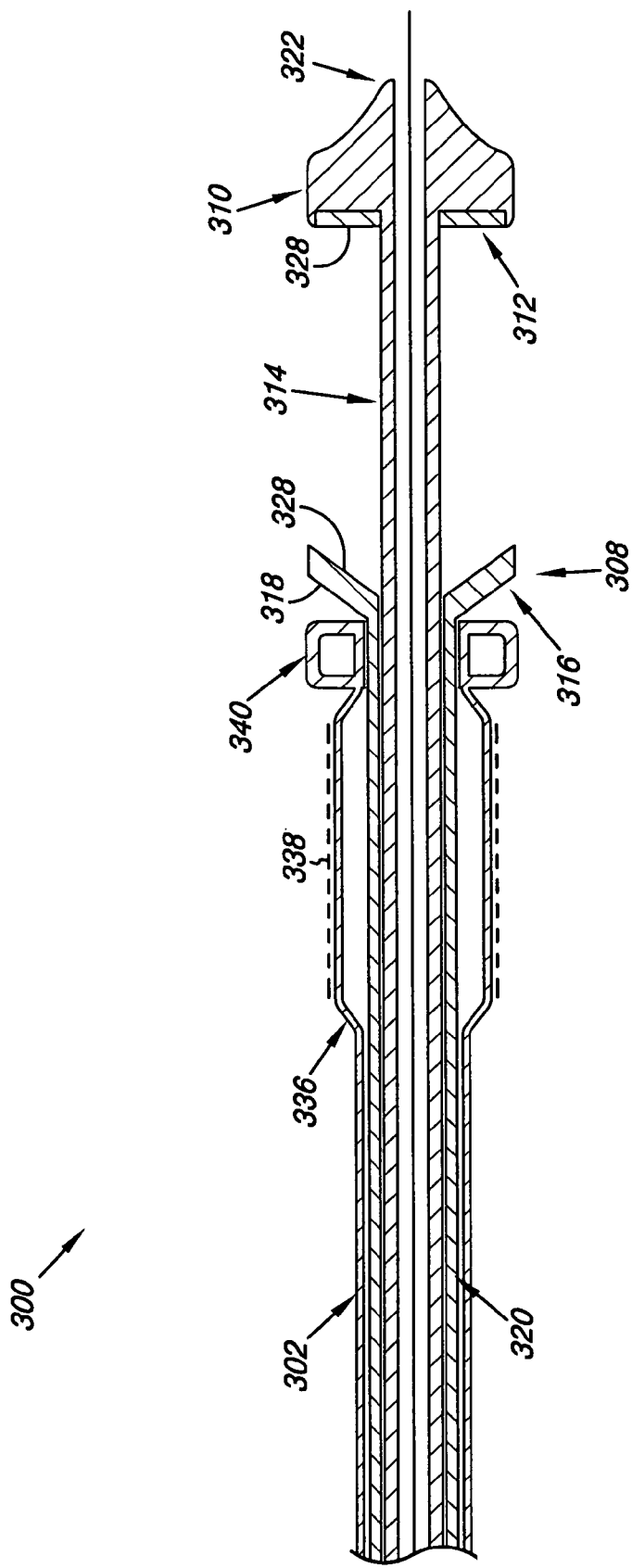
FIG. 3 illustrates the embodiment of the catheter of FIG. 2 in a sectional view taken along line 3-3 in FIG. 2.

FIG. 3 provides a cross-sectional view of the catheter 300 taken along lines 3-3 in FIG. 2.

Figure 4:
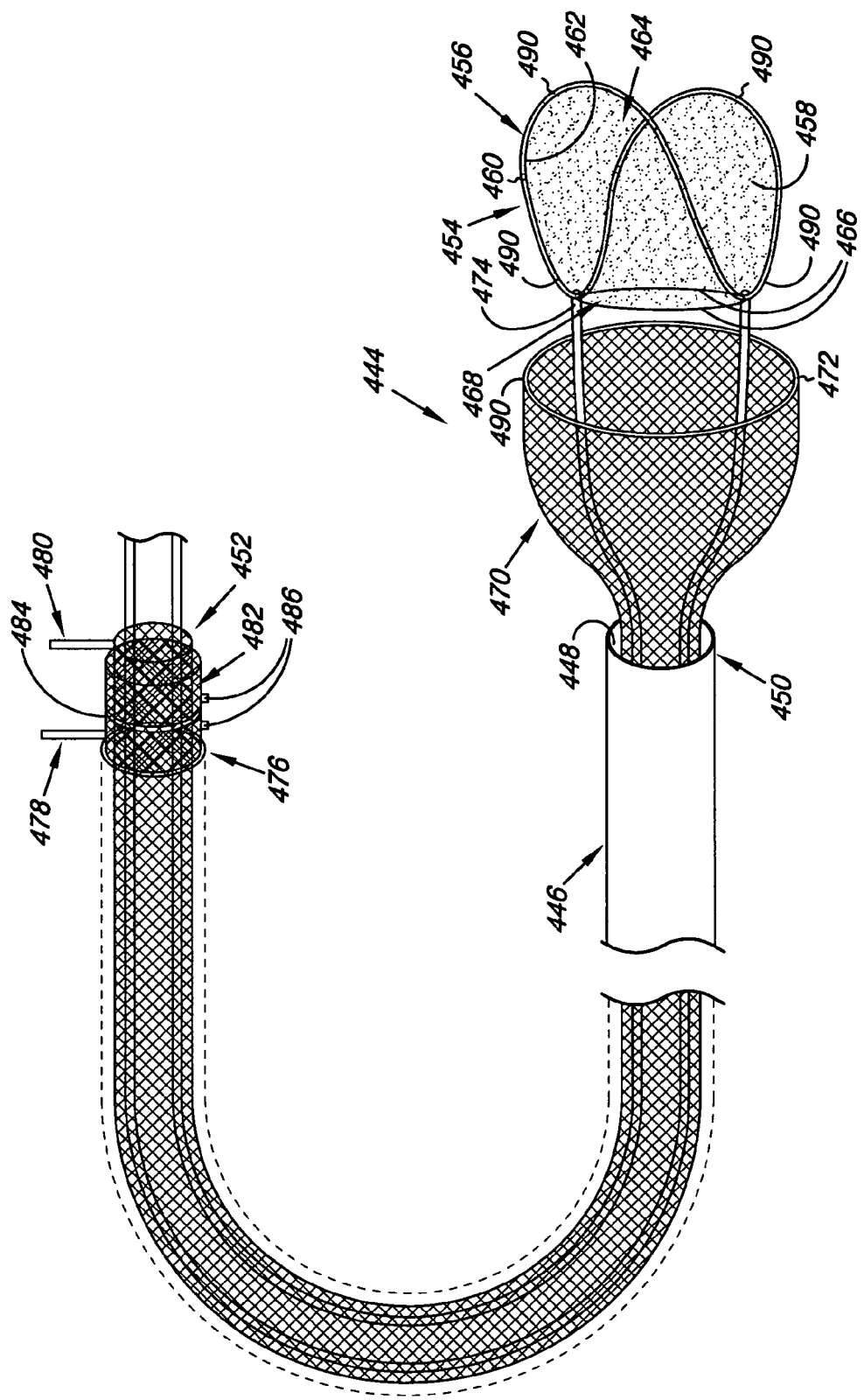
FIG. 4 illustrates an embodiment of an apparatus in perspective view having partial sectional views to show detail.

FIG. 4 provides an illustration of an apparatus 444 that can be used in conjunction with the catheter 100/200. In one embodiment, apparatus 444 includes a sheath 446 having a lumen 448. The sheath 446 includes a first sheath end 450 and a second sheath end 452. In one embodiment, at least part of the elongate body 102/202 can reside in the lumen 448 of the sheath 446, as will be illustrated herein.

The apparatus 444 can further include a cardiac valve 454. The cardiac valve 454 can be releasably positioned within the lumen 448 of the sheath 446. Generally, valve 454 can be implanted within the fluid passageway of a body lumen, such as for replacement of a valve structure within the body lumen (e.g., a venous valve), to regulate the flow of a bodily fluid through the body lumen in a single direction.

With respect to the apparatus 444, the cardiac valve 454 can be configured to reside in a compressed state within the lumen 448 of the apparatus 444. When released from the lumen 448, the cardiac valve 454 expands into a deployed state as illustrated in FIG. 4. In one embodiment, the cardiac valve 454 expands from its compressed state within the lumen 448 to the deployed state when the sheath 446 is retracted from around the valve 454.

The cardiac valve 454 further includes a support frame 456 and a cover 458. The support frame 456 can include an outer surface 460, an inner surface 462 defining a lumen 464. The configuration of the support frame 456 provides the valve 454 with sufficient flexibility to move between the compressed and the deployed states.

The cover 458 of the cardiac valve 454 can be positioned over at least the outer surface 460 of the support frame 456. In one embodiment, the cover 458 includes surfaces 466 defining a reversibly sealable opening 468 for unidirectional flow of a liquid through the lumen 464 of the cardiac valve 454. For example, surfaces of the cover 458 can be deflectable between a closed configuration in which fluid flow through the lumen 464 can be restricted and an open configuration in which fluid flow through the lumen 464 can be permitted. One example of cardiac valve 446 includes those described in U.S. Patent application Ser. No. 11/052,655 entitled "Venous Valve Apparatus, System, and Method", which is incorporated herein by reference in its entirety.

The support frame 456 can be formed from any number of materials. For example, the support frame 456 can be formed from a biocompatible metal, metal alloy, polymeric material, or combination thereof. Examples of suitable materials include, but are not limited to, medical grade stainless steel (e.g., 316L), titanium, tantalum, platinum alloys, niobium alloys, cobalt alloys, alginate, or combinations thereof. In an additional embodiment, the support frame 456 may be formed from a shape-memory material, such as shape memory plastics, polymers, and thermoplastic materials which are inert in the body. Shaped memory alloys having superelastic properties generally made from specific ratios of nickel and titanium, commonly known as nitinol, are also possible materials. Other materials are also possible.

In one embodiment, the material of the cover 458 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethylene (PE), polyethylene terephthalate (PET), silk, urethane, Rayon, Silicone, or the like. Possible biologic materials include, but are not limited to, autologous, allogeneic or xenograft material. These include explanted veins and decellularized basement membrane materials, such as small intestine submucosa (SIS) or umbilical vein.

The support frame 456 of the cardiac valve 454 expands to increase a diameter of the lumen 464 as the sheath 446 moves relative the cardiac valve 454 and an expandable filter 470 to deploy the cardiac valve 454. In one embodiment, the size of lumen 464 can be determined based upon the type of body lumen and the body lumen size in which the valve 454 is to be placed. In an additional example, there can also be a minimum value for the width for the support frame 456 that ensures that the valve 454 will have an appropriate expansion force against the inner wall of the body lumen to encourage fixation of the valve 454 and to prevent retrograde flow within the body lumen. Anchoring elements (e.g., barbs) can also be included on the support frame 456 of the valve 454.

The apparatus can further include the expandable filter 470 positioned within the lumen 448 of the sheath 446. In one embodiment, the expandable filter 470 can be positioned coaxially with the sheath 446. The expandable filter 470 includes a first filter end 472 adjacent the first sheath end 450. In one embodiment, the first filter end 472 has a first diameter when positioned between the sheath 446 that expands to a second diameter when the sheath 446 moves along a longitudinal axis relative the cardiac valve 454 and the expandable filter 470 to deploy the cardiac valve 454 and at least the first filter end 472. FIG. 4 provides an illustration of sheath 446 having been retracted to deploy the cardiac valve 454 and at least partially deploy the expandable filter 470.

In one embodiment, the expandable filter 470 radially self-expands as the sheath 446 is retracted. For example, the expandable filter 470 can be configured to expand from a compressed state within the lumen 448 of the sheath 446 into an expanded state as the sheath 446 is retracted from the expandable filter 470. The expandable filter 470 in its deployed state can fill the cross-section area of the lumen in which the expandable filter 470 is deployed. In addition, filter 470 in its deployed state can apply sufficient pressure to the inner wall of the lumen to reduce the volume of fluid (e.g., blood) that may pass between the filter 470 and the surface of the lumen wall. As will be appreciated, the area and shape defined by the expandable filter 470 (e.g., the diameter of the expandable filter) in its deployed state will be dependent upon the location in which the apparatus is intended to be used.

The first filter end 472 can also be configured to extend proximally and distally in a curvilinear manner (i.e., a multi-lobe configuration) to accommodate the valve 454 configuration and the dissected valve anatomy. In addition, this first filter end 472 configuration may also allow filter protection of the cononary ostia while maximizing working area for valve repair or replacement.

Examples of radially self-expanding filters include those formed from temperature-sensitive memory alloy which changes shape at a designated temperature or temperature range. Examples of such materials include, but are not limited to, nitinol and nitinol-type metal alloys. Alternatively, self-expanding filters can include those having a spring-bias imparted into the members forming the filter 470. The expandable filter 470 can have a woven and/or a knit configuration that can also impart a self-expanding aspect to the expandable filter 470. The expandable filter 470 can also include a self-expanding component in addition to more passive porous filtering material which controls filtering size while the self-expanding component provides the deployment motion. Such filtering material can be, for example, woven, braided, knit, machined, matted, expanded, or other configurations as are known, or will be known, in polymer and textile processing.

The apparatus 444 further includes a retention line 474 releasably coupled to the support frame 456. The retention line 474 extends from the cardiac valve 454 through the lumen 448 of the sheath 446. In one embodiment, the retention line 474 can be used to move the cardiac valve 454. For example, the retention line 474 can extend through the lumen 448 past a proximal end of the sheath 446 where the line 474 can be used to draw the cardiac valve 454 at least partially back into its compressed state within the lumen 448 of the sheath 446. Alternatively, the retention line 474 can be used to change the position of the cardiac valve 454 once deployed from a first position within the lumen to a second position. The retention line 474 can be optionally removed from the valve 454 by drawing one end of the line 474 through the valve 454.

The sheath 446 can be formed of a number of materials. Materials include polymers, such as PVC, PE, POC, PET, polyamid, mixtures, and block co-polymers thereof. In addition, the sheath 446 can have a wall thickness and an inner diameter sufficient to maintain both the cardiac valve 454 and the expandable filter 470 in compressed states when they are positioned within the lumen 448.

The apparatus 444 can further include handles positioned at a proximal end 376 of the sheath 446 and the expandable filter 470. In one embodiment, the sheath 446 includes a handle 478 and the expandable filter 464 includes a handle 480. Handles 478 and 480 allow the sheath 446 to be retracted from the proximal end 476 to expose and expand the valve 454 and at least a part of filter 470. In one embodiment, the distance between the handles 478 and 480 can correspond approximately to the length of the compacted cardiac valve 454 and at least a portion of the filter 470.

Figure 5:
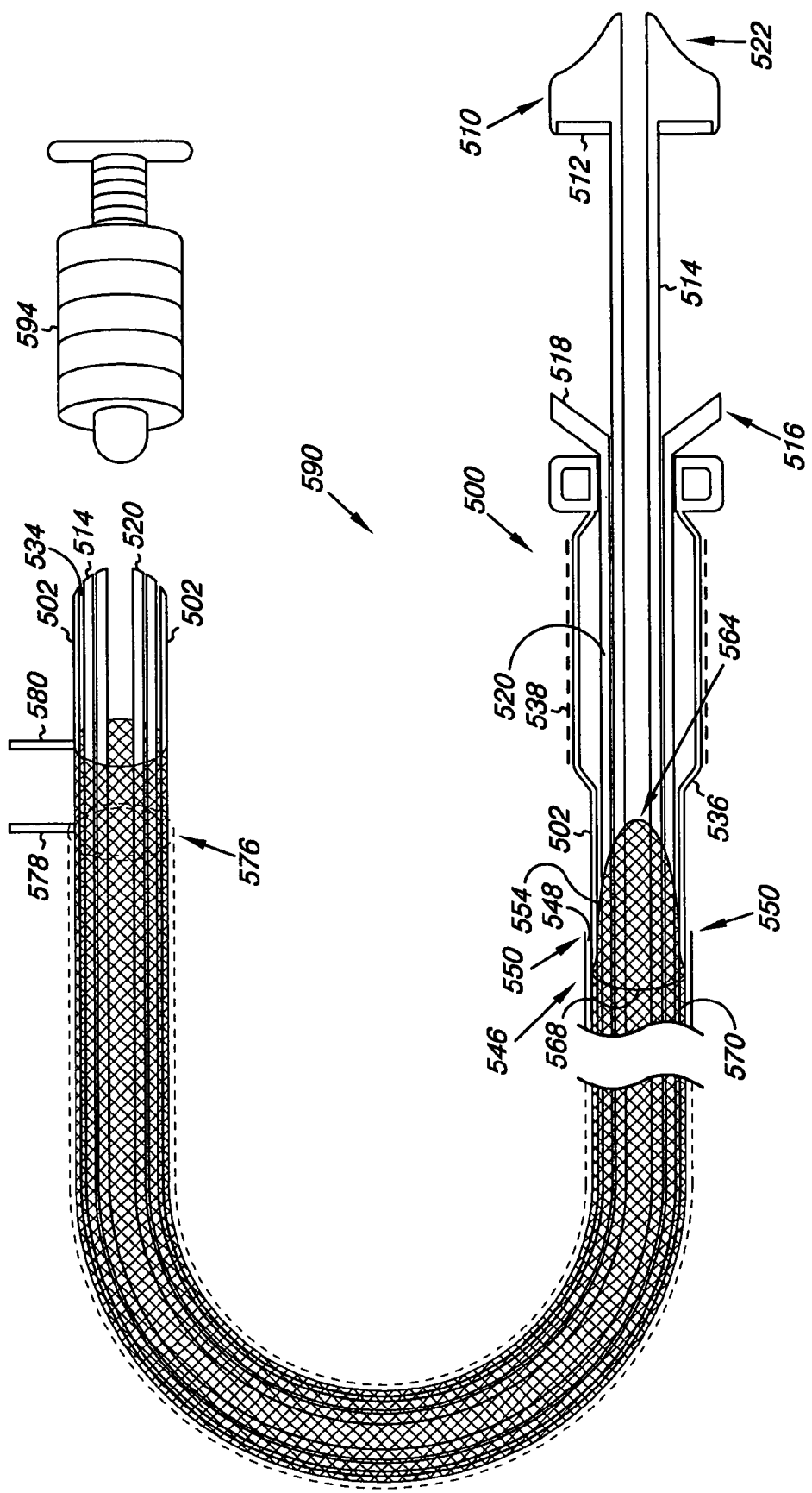
FIG. 5 illustrates an embodiment of a system including a catheter and an apparatus in perspective view having partial sectional views to show detail.

In an additional embodiment, the apparatus 440 can further include a sleeve 482 having a slit 484 and a pull tab 486 positioned between the handles during delivery to prevent inadvertent exposure of the cardiac valve 454 and filter 470 (FIG. 5). For example, the sleeve 482 can be stripped from the apparatus 440 once the apparatus 440 has been placed at the predetermined location at which the cardiac valve 446 and the filter 464 are to be deployed. Other removable structures for preventing inadvertent exposure of the cardiac valve 454 and filter 470 are also possible.

In an additional embodiment, the apparatus 444 can further include radiopaque markers 490. For example, radiopaque markers (e.g., attached or coated) can be used to mark the location of the cardiac valve 454 and/or the expandable filter 470. Other portions of catheter apparatus 444 can also be marked with radiopaque markers as necessary to allow for visualization of the location and position of parts of the apparatus 444.

FIG. 5 provides an illustration of one embodiment of a system 590 that include both the catheter 500 and the apparatus 544. As illustrated in FIG. 5, the elongate body 502 of catheter 500 can be positioned at least partially within the lumen 548 of the sheath 546. In one embodiment, the elongate body 502 passes through and can move longitudinally within the lumen of the expandable filter 570 and the reversibly sealable opening 568 of the cardiac valve 554.

In an additional embodiment, the first sheath end 550 can be positioned between the inflatable balloon 536 and the second sheath end 576. As discussed, the sheath 546 can be moved relative the cardiac valve 554 and the expandable filter 570 to deploy the cardiac valve 554 and at least a portion of the expandable filter 570 proximal the inflatable balloon 536 and the expandable stent 538. The system 590 further includes an inflation device 594 that can reversibly couple in fluid tight communication with the second lumen 534 to provide fluid pressure to inflate and deflate balloon 536. After the procedure, the expandable filter 570 can be withdrawn together with any captured debris.

The embodiments of the present invention further include methods for forming the catheters, apparatus and systems, as discussed herein. For example, embodiments of the catheters of the present invention can be formed by providing an elongate body having a first lumen and a second lumen extending between the proximal end and the distal end of the elongate body. The first cutting head with its blade can then be positioned proximal the distal end of the elongate body. In one embodiment, the first cutting head includes the elongate pulling member positioned within the first lumen of the elongate body. The elongate pulling member extends through the first lumen such that the elongate pulling member can slide within the first lumen to move the first cutting head relative the distal end of the elongate body.

The catheter can further include the second cutting head having its blade positioned adjacent the distal end of the elongate body between the distal end and the first cutting head. In one embodiment, the second cutting head includes the elongate pushing member extending through the first lumen such that the elongate pushing member can slide within the first lumen to move the second cutting head relative the distal end of the elongate body and the first cutting head. As discussed herein, the blades of the first cutting head and the second cutting head move relative each other to provide the shearing action.

The catheter can also include the inflatable balloon positioned adjacent the distal end of the elongate body and proximal to the second cutting head. The expandable balloon member can be in fluid tight communication with the second lumen. The expandable stent can then be positioned over at least a portion of the inflatable balloon. In an additional embodiment, the catheter can further include positioning the annular push ring between the second cutting head and the inflatable balloon of the catheter.

The embodiments of the catheter can also be combined with the embodiments of the apparatus to form embodiments of the system of the present invention. For example, embodiments of the apparatus can be formed by positioning both the expandable filter and the cardiac valve in the lumen of the sheath, as illustrated herein. The lumen of the sheath can then also be positioned over and adjacent to at least part of the elongate body. The sheath can then move relative the cardiac valve and the expandable filter to deploy the cardiac valve and at least a portion of the expandable filter proximal the inflatable balloon and the expandable stent.

The embodiments of the catheter, apparatus and system described herein may be used to replace, supplement, or augment valve structures within one or more lumens of the body. For example, embodiments of the present invention may be used to replace an incompetent cardiac valve of the heart, such as the aortic, pulmonary and/or mitral valve of the heart.

In one embodiment, the method of replacing, supplementing, and/or augmenting a valve structure can include positioning at least part of the catheter of the system at a predetermined location within an artery of a patient, such as in the aorta adjacent the root of the aortic valve. In positioning the catheter, first and second cutting heads can be positioned with the cardiac valve leaflets (e.g., leaflets of and aortic valve) between the blades of the cutting heads.

The sheath of the apparatus can then be retracted so as to deploy both the cardiac valve and the expandable filter. The cutting heads can then be used to shear the cardiac tissue of the valve leaflets. The catheter can then be advance so that the annular push ring contacts and directs the sheared cardiac tissue in the same direction. The stent can then be deployed over the sheared cardiac tissue (e.g., the sheared aortic leaflets) to position them between the stent and the wall of the lumen. The retention lines can then be withdrawn, along with the expandable filter through the lumen of the sheath. Finally, the deflated balloon, annular push ring, and cutting heads of the catheter can be drawn through the lumen of the expanded cardiac valve and out of the lumen.

In one embodiment, positioning the system within the body lumen includes introducing the system into the cardiovascular system of the patient using minimally invasive percutaneous, transluminal catheter based delivery system, as is known in the art. For example, a guidewire can be positioned within the cardiovascular system of a patient that includes the predetermined location. The system (e.g., apparatus and catheter) can be positioned over the guidewire and the system advanced so as to position the cutting heads, stent, and valve on or adjacent to the predetermined location. In one embodiment, radiopaque markers on the various elements of the system, as described herein, can be used to help locate and position the system.

Both the stent and the valve can be deployed from the system at the predetermined location in any number of ways, as described herein. In one embodiment, the stent and the valve of the present invention can be deployed and placed in any number of cardiovascular locations. For example, the stent and the valve can be deployed and placed within a major artery of a patient. In one embodiment, major arteries include, but are not limited to, the aorta. In addition, valves of the present invention can be deployed and placed within other major arteries of the heart and/or within the heart itself, such as in pulmonary artery for replacement and/or augmentation of the pulmonary valve and between the left atrium and the left ventricle for replacement and/or augmentation of the mitral valve. Other locations are also possible.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow the valve to exert a force on the body lumen wall and accommodate changes in the body lumen diameter, while maintaining the proper placement of the valve. As described herein, the valve can engage the lumen so as to reduce the volume of retrograde flow through and around the valve. It is, however, understood that some leaking or fluid flow may occur between the valve and the body lumen and/or through the valve leaflets.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the stent 238, support frame 356 and/or the cover 358 can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system, comprising:
   an elongate catheter body having a first lumen and a second lumen extending between a proximal end and a distal end of the elongate catheter body;
   a first cutting head having a blade and an elongate pulling member, the elongate pulling member extends through the first lumen and slides within the first lumen to move the first cutting head relative to the distal end of the elongate catheter body;
   a second cutting head having a blade, the second cutting head positioned adjacent to the distal end of the elongate catheter body between the distal end and the first cutting head;
   an inflatable balloon positioned adjacent to the distal end of the elongate catheter body and proximal to the second cutting head, the inflatable balloon in fluid tight communication with the second lumen;
   an expandable stent positioned over at least a portion of the inflatable balloon, where the blade of the first cutting head moves relative to the blade of the second cutting head to provide a shearing action for cardiac tissue and the inflatable balloon deploys the expandable stent over sheared cardiac tissue; and
   an expandable filter positioned within a lumen of a sheath and proximal to a cardiac valve, wherein the elongate catheter body is positioned at least partially within the lumen of the sheath, and wherein the sheath moves relative to the cardiac valve and the expandable filter to deploy the cardiac valve and at least a portion of the expandable filter and wherein both the cardiac valve and the expandable filter are positioned toward the proximal end relative to the inflatable balloon and the expandable stent.

2. The system of claim 1, wherein the first cutting head includes a first end and a second end, the second end having the blade with a cutting edge, and wherein the second cutting head includes the blade with a cutting edge in alignment with the cutting edge of the blade of the first cutting head, the first cutting head moving relative to the second cutting head to slide the first cutting edge past the second cutting edge.

3. The system of claim 2, wherein the first cutting head has a conical shape with the first end having a diameter less than the second end.

4. The system of claim 1, the second cutting head further including an elongate pushing member, wherein elongate pushing member slides within the first lumen to move the second cutting head relative to the distal end of the elongate body and the first cutting head, the elongate pulling member arranged concentrically with the elongate pushing member in the first lumen.

5. The system of claim 1, further including an annular push ring positioned between the second cutting head and the inflatable balloon for contacting and moving at least a portion of the sheared cardiac tissue.

6. The system of claim 1, wherein a support frame of the cardiac valve expands to increase a diameter of a lumen defined by the cardiac valve as the sheath moves relative to the cardiac valve and the expandable filter to deploy the cardiac valve.

7. The system of claim 1, further including a retention line releasably coupled to the support frame, wherein the retention line extends through the lumen of the sheath past the proximal end of the elongate body.

8. The system of claim 1, wherein the sheath includes a first sheath end and a second sheath end, the first sheath end positioned between the inflatable balloon and the second sheath end, and wherein the expandable filter includes a first filter end adjacent the first sheath end, the first filter end having a first diameter when positioned between the sheath and the elongate body that expands to a second diameter when the sheath moves relative the cardiac valve and the expandable filter to deploy at least the first filter end.

9. A system, comprising:
   an elongate catheter body having a first lumen and a second lumen extending between a proximal end and a distal end of the elongate catheter body;
   a first cutting head having a blade and an elongate pulling member, wherein the elongate pulling member extends through the first lumen and slides within the first lumen to move the first cutting head relative to the distal end of the elongate catheter body;
   a second cutting head having a blade, the second cutting head positioned adjacent to the distal end of the elongate catheter body between the distal end and the first cutting head; and
   an expandable filter positioned within a lumen of a sheath proximal to a cardiac valve, wherein the elongate catheter body is positioned at least partially within the lumen of the sheath, and wherein the sheath moves relative to the cardiac valve and the expandable filter to deploy the cardiac valve and at least a portion of the expandable filter and wherein both the cardiac valve and the expandable filter are positioned toward the proximal end relative to an inflatable balloon and an expandable stent.

10. A system, comprising:
    an elongate catheter body having a first lumen and a second lumen extending between a proximal end and a distal end of the elongate catheter body;
    a first cutting head having a blade and an elongate pulling member wherein the elongate pulling member extends through the first lumen and slides within the first lumen to move the first cutting head relative to the distal end of the elongate catheter body;
    a second cutting head having a blade, the second cutting head positioned adjacent to the distal end of the elongate catheter body between the distal end and the first cutting head; and
    an expandable filter positioned within a lumen of a sheath and proximal to a cardiac valve, wherein the elongate catheter body is positioned at least partially within the lumen of the sheath, and where the cardiac valve is releasably positioned within the lumen of the sheath and the elongate catheter body extends through a lumen of the cardiac valve, wherein the sheath can move relative to the cardiac valve and the expandable filter to deploy the cardiac valve and at least a portion of the expandable filter and where both the cardiac valve and the expandable filter are positioned toward the proximal end relative to an inflatable balloon positioned adjacent the distal end of the elongate catheter body and proximal to the second cutting head and an expandable stent.

* * * * *